(12) United States Patent
de Jong

(10) Patent No.: US 9,180,195 B2
(45) Date of Patent: Nov. 10, 2015

(54) CONTROLLED RELEASE GELS

(75) Inventor: Menno R. de Jong, Groningen (NL)

(73) Assignee: Nano Fiber Matrices B.V., Groningen (NL)

( * ) Notice: Subject to any disclaimer, the term of this patent is extended or adjusted under 35 U.S.C. 154(b) by 1067 days.

(21) Appl. No.: 12/087,039

(22) PCT Filed: Dec. 22, 2006

(86) PCT No.: PCT/NL2006/000664
§ 371 (c)(1),
(2), (4) Date: Feb. 4, 2009

(87) PCT Pub. No.: WO2007/073180
PCT Pub. Date: Jun. 28, 2007

(65) Prior Publication Data
US 2009/0169498 A1    Jul. 2, 2009

(30) Foreign Application Priority Data
Dec. 23, 2005  (EP) .................................. 05077973

(51) Int. Cl.
*A61K 8/00*   (2006.01)
*A61K 47/18*  (2006.01)

(52) U.S. Cl.
CPC .................................. *A61K 47/183* (2013.01)

(58) Field of Classification Search
CPC ......... A61K 9/14; A61K 9/1688; A61K 8/18; A61K 38/00; A61K 39/395; A61K 39/00; A61K 31/56; A61K 31/7088; A61K 51/00; B01J 2/08; A61Q 19/02
See application file for complete search history.

(56) References Cited

U.S. PATENT DOCUMENTS

2006/0099270 A1*  5/2006  Friggeri et al. ............... 424/489

FOREIGN PATENT DOCUMENTS

| EP | 0945452 A1 | 11/1997 | |
| WO | WO 93/23008 | 11/1993 | |
| WO | WO 03/097587 A2 | 11/2003 | |
| WO | WO 2004/103347 | * 12/2004 | ............... A61K 9/14 |
| WO | WO 2004/103347 A | 12/2004 | |
| WO | WO 2005/047231 A1 | 5/2005 | |
| WO | WO 2005/080477 A | 9/2005 | |
| WO | WO 2007/073180 A1 | 6/2007 | |

OTHER PUBLICATIONS

Sigma Product Sheet for MethylCellulose (available online Jun. 3, 1997), Sigma Catalog, 1997, pp. 1-5.*
Hanabusa et al., Easy Preparation and Useful Character of Organogel Electrolytes Based on Low Molecular Weight Gelator, Chem. Mater., 1999, pp. 649-655, vol. 11.
Low tack styling gel with Allianz, Happi, Mar. 2001, p. 18.
Wave set, Happi, Jul. 2002, p. 20.
Extreme hold gel, Firm hold non aerosol hair spray, Happi, Dec. 2002, pp. 18, 20.
Lipid-replenishing microemulsion styling gel, Happi, Jun. 2003, p. 16.
PCT International Search Report, PCT/NL2006/000664, dated Apr. 13, 2007.
Osol et al., (editors) Remington's Pharmaceutical Sciences, Sixteenth Edition, 1980, Terminology, pp. 1596-1597.
Hanabusa, et al., Easy Preparation and Useful Character of Organogel Electrolytes Based on Low Molecular Weight Gelator, Chem. Mater, 1999, pp. 649-655, vol. 11.

* cited by examiner

*Primary Examiner* — Suzanne Ziska
(74) *Attorney, Agent, or Firm* — TraskBritt, P.C.

(57) ABSTRACT

Described are gel-based delivery systems for a compound of interest, like a drug or cosmetic agent. Described is a gel comprising at least one non-polymeric gelator and at least one polymer, wherein the polymer content of the gel is more than 5 weight percent (wt %), preferably at least 10 wt %, and more preferably at least 20 wt %. Also provided are a method for preparing the gel and a method of using the gel in a controlled delivery system, for example, a pH-sensitive drug delivery system.

22 Claims, 3 Drawing Sheets

CONTROLLED RELEASE GELS

Figure 1:
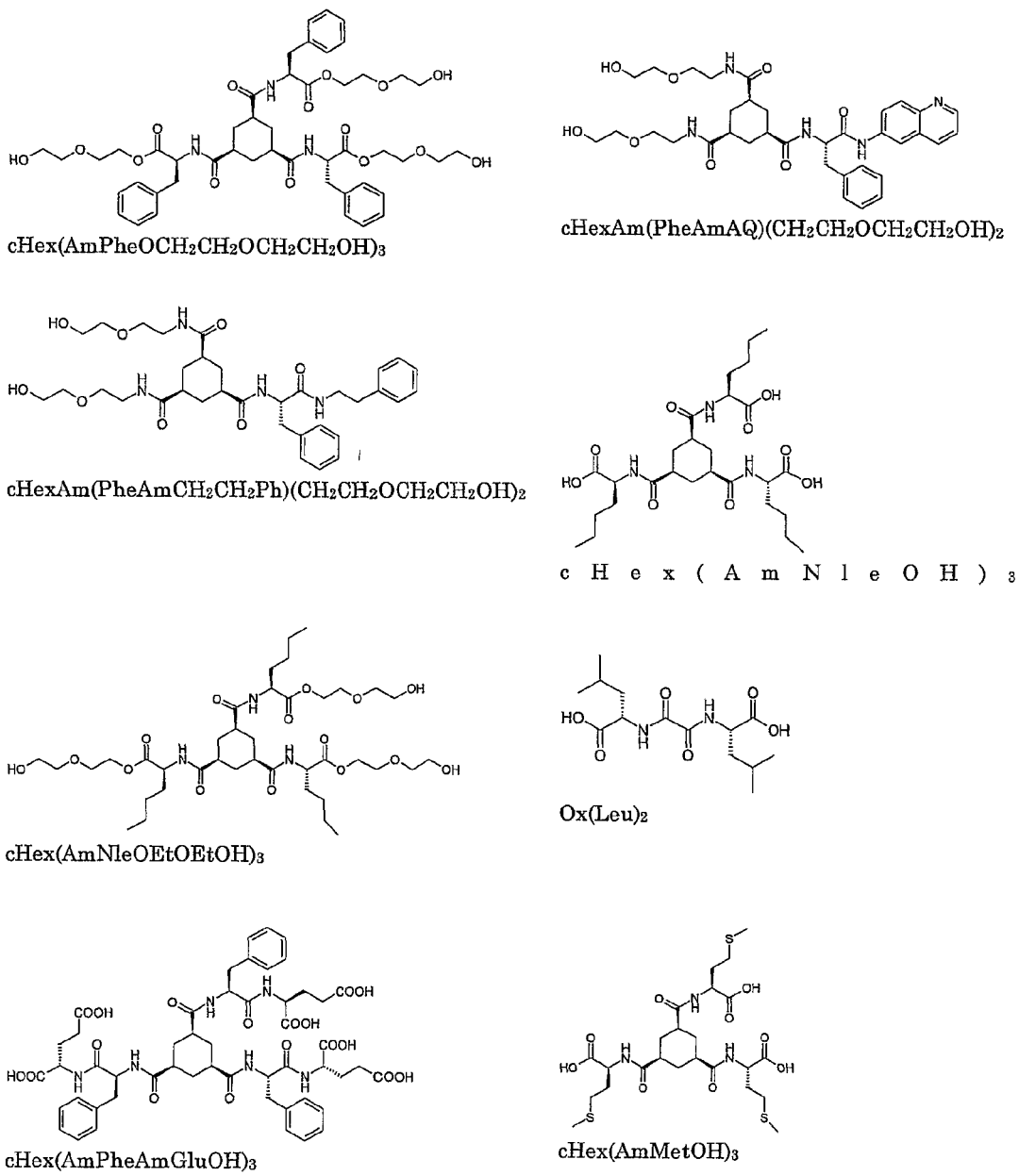

The invention relates to the field of gel-based delivery systems for a compound of interest, like a drug or cosmetic agent. Among others, it relates to gels comprising a nonpolymeric, low molecular weight gelator and a polymer. The gels are particularly suitable for use in a controlled delivery system.

For long, pharmaceuticals have primarily consisted of simple, fast-acting chemical compounds that are dispensed orally (as solid pills and liquids) or as injectables. During the past three decades, however, formulations that control the rate and period of drug delivery (i.e., time-release medications) and target specific areas of the body for treatment have become increasingly important. Also for cosmetics, a slow or sustained release of an active agent can be desirable.

Controlled drug delivery occurs when a delivery vehicle is judiciously combined with a drug or other active agent in such a way that the active agent is released from the material in a predesigned manner. The release of the active agent may be constant over a long period, it may be cyclic over a long period, or it may be triggered by the environment or other external events. In any case, the purpose behind controlling the drug delivery is to achieve more effective therapies while eliminating the potential for both under- and overdosing. Other advantages of using controlled-delivery systems can include the maintenance of drug levels within a desired range, the need for fewer administrations, optimal use of the drug in question, and increased patient compliance.

One of the central problems in drug delivery today is striking the balance between toxicity and therapeutic effect of pharmaceuticals. By limiting the delivery to specific target sites, possible toxic effects at non-target sites can be avoided and the efficiency of the drug is increased. For this reason, controlled drug delivery systems have been a major focus of pharmaceutical and materials research (for review see Razzacki et al. Adv. Drug. Deliver. Rev., 2004, 56, 185-198 or Kopecek et al., Eur. J. Pharm. Sci., 2003, 20, 1-161).

Providing control over drug delivery can be the most important factor at times when traditional oral or injectable drug formulations cannot be used. These include situations requiring the slow release of water-soluble drugs, the fast release of low-solubility drugs, drug delivery to specific sites, drug delivery using nanoparticulate systems, delivery of two or more agents with the same formulation, and systems based on carriers that can dissolve or degrade and be readily eliminated. For example, many drugs' potencies and therapeutic effects are limited or otherwise reduced because of the (partial) degradation that occurs before they reach a desired target in the body. The ideal drug delivery system should be inert, biocompatible, mechanically strong, comfortable for the patient, capable of achieving high drug loading, safe from accidental release, simple to administer and remove, and easy to fabricate and sterilize.

Recently, the potential of low molecular weight gelator (LMWG) gels for controlled (drug) release systems was demonstrated. Gels of low molecular LMWGs are self-assembled, thermoreversible, viscoelastic materials which can be rendered sensitive to light, pH or chemical substances by simple chemical modifications. In addition, the ability of some of these LMWGs to gelate water (hydrogelators) makes these gels interesting, new materials for e.g. drug delivery applications. Friggeri, A. et al. (2004, Journal of Controlled Release, Vol. 97, No. 2, pages 241-248) were the first to report a drug release study from LMWG gels. It concerned the release of small (model) drug molecules: 8-aminoquinoline (AQ) and 2-hydroxyquinoline (HQ), from gels of the nopolymeric gelator N,N'-dibenzoyl-L-cystine (DBC). The complete release of the model drugs from the LMWG gels was found to be in the order of approximately 15 min (HQ) to 1 hr (AQ). Furthermore, the initial release rate of HQ was approximately seven times faster than that of AQ and the initial release of the latter follows the kinetics of gel degradation. These results indicate the potential of LMWG gels as delivery vehicles for small drug molecules and also show that the release profiles for such systems can be fine-tuned by the correct choice of gelator-drug combination. The potential of LMWG systems for the development of drug delivery devices was confirmed in a subsequent study by Van Bommel et al. (Organic & Biomolecular Chemistry, 2005, 3(16), 2917-2920), reporting an enzymatically cleavable low molecular weight gelator-(model) drug conjugate system which can be employed to effect a two-step enzyme mediated drug release. Incorporation of the drug into the gel fibers protects molecules from enzymatic cleavage. Upon applying a stimulus (e.g., via a pH or temperature change) these gel fibers dissociate into individual molecules that can be cleaved by the enzyme, resulting in a two-step release mechanism for drugs.

Hence, gels of LMWGs can have rapid response times, in the order of a few seconds, that are not attainable by conventionally studied polymeric systems (J. C. Tiller, Angew. Chem., Int. Ed., 2003, 42, 3072-3075). Furthermore, the release can be controlled by external stimuli.

However, the use of LMWG gels in slow or sustained release systems has thus far been limited. The preparation of slow release LMWG gels has been hampered due to the limited solubility of many gelators and/or to the poor network forming capabilities of others. So far, gels with a network density that is suitable for slow release systems have been difficult to make using conventional methods, including solvent change or temperature quench methods.

It is therefore an object of the present invention to provide a LMWG system that shows slower release profiles as compared to existing LMWG systems, preferably independent of the choice of gelator-drug combination. In particular, it is an object to provide a slow release gel based on LMWGs that allows for controlled release, such as after a change in pH or other type of external trigger.

These goals are met by the surprising finding that the addition of a polymer to a LMWG gel leads to a gel with a dense network, strengthening the overall gel structure and slowing down diffusion and release of (dissolved) species initially enclosed in the gel. LMWG gels comprising a polymer have a significantly slower release profile, than what is observed in the absence of the polymer. For example, the initial release of a compound from a gel was reduced from about 80% after 15 minutes to 30% after 15 min upon the incorporation of 20 wt % of a polymer in the gel. A gel comprising an acidic gelator in combination with a polymer was evaluated in simulated gastric fluid (pH 1.2) and found to be particularly suitable for delayed drug release in an acidic environment. Without wishing to be bound by theory it is believed that the combination of a LMWG and a suitable polymer leads to the immobilization or entanglement of the polymer chains within the gel network, hence providing for a much denser gel structure in which diffusion becomes limited.

Accordingly, the invention provides a gel comprising at least one nonpolymeric gelator and at least one polymer. As is exemplified in the Examples below, the release rate of a compound enclosed in a gel was found to be inversely correlated with the amount of polymer present in the gel. The total polymer content of a gel is preferably more than 5 weight percent (wt %) to ensure a sufficiently dense gel network. In one embodiment, the gel contains at least 6 wt %, like 7, 8 or 9 wt % polymer. Preferably, the gel comprises at least 10 wt % polymer, like 12 or 15 wt % more preferably at least 20 wt %. Gels with very good release profiles were obtained using an even higher polymer content, for instance 25, 30, 35, 40, 50, 55 wt % polymer. There is no absolute maximum with respect to the polymer content of a gel according to the invention. Typically, the solubility of a particular polymer used will determine how much can be incorporated in the gel. In one embodiment, the total concentration of polymer in said gel is in the range of 6-70 wt %, preferably 7-60 wt %, more preferably 10-50 wt %.

Various types of polymers can be used to prepare a controlled release LMWG gel of the invention. Also, combinations of two or more different polymers can be used. The polymer preferably has a molecular weight of at least 500 Dalton, preferably at least 1 kiloDalton (kDa), more preferably at least 1.5 kDa, most preferably at least 3 kDa. Without wishing to be bound by theory, it is believed that the higher the molecular weight of the polymer, the interactions which take place among the polymer chains are stronger and less influenced by the solvent. This results in a reduced release of the entrapped compound(s). The polymer can be a grafted, a branched or a linear polymer. In a preferred embodiment, a gel comprises a linear polymer or a combination of a linear polymer and a branched polymer. In one aspect, the polymer is a non-gelating polymer.

In one aspect, for example if the gel is to be applied in vivo, it is preferred that the polymer is a biocompatible polymer. It can be biodegradable or non-biodegradable.

In one embodiment, a slow release LMWG gel comprises at least one biodegradable polymer selected from the group consisting of polylactides, polyglycolides, polylactics, polylactic acid-co-glycolic acid, polylactide-co-glycolides, polyesteramides, star-branched polymers, polyphosphoesters, albumin, fibrin, fibrinogen combinations, polycaprolactones, polydioxanones, polycarbonates, polyhydroxybutyrates, polyalkylene oxalates, polyanhydrides, polyamides, polyurethanes, polyacetals, polyketals, polyorthocarbonates, polyphosphazenes, polyhydroxyvalerates, polyalkylene succinates, poly(malic acid), poly(amino acids), chitin, chitosan, polyorthoesters, gelatin, collagen, polyethylene glycols, polyethylene oxides, polypropylene oxides, polyethers, beta-cyclodextrin, polysaccharides, polyvinyl alcohol, polyvinyl pyrrolidone, polyvinyl-alcohol, polyoxyethylene-polypropylene block copolymers, and their copolymers, terpolymers and combinations and mixtures thereof.

Alternatively, or in addition, a gel the invention comprises at least one nonbiodegradable polymer selected from the group consisting essentially of ethyl celluloses, acrylates, methacrylates, pyrrolidones, polyoxyethylenes, polyoxyethylene-polypropylene copolymers, hydroxypropylmethyl celluloses, hydroxypropyl celluloses, methyl celluloses, polymethylmethacrylates, cellulose acetates and their derivatives, shellac, methacrylic acid based polymers, their copolymers, combinations and mixtures thereof.

The polymer can, but does not have to be water soluble. Water soluble polymers (WSPs) represent a diverse and varied group of chemicals. Nearly every industrial sector uses WSPs during some phase of its operation. Unfortunately, this has discouraged a unified, coherent set of nomenclature. Indeed, substances identified as water soluble polymers by one industrial sector may not be considered water soluble polymers by a different sector. WSPs can be classified by derivation, chemical structures, and application. They are derived from natural sources (gums, proteins, celluloses, starches, etc.), from wholly synthetic sources (polyvinyls, polyacrylates, polyimines, petroleum sulfonates, etc.), and semi-synthetic sources formed by modifying natural materials to produce forms with more desirable properties. According to the present invention, a material will be considered a water soluble polymer if: 1) it contains at least 10 monomer units in the polymer chain, 2) it forms an aqueous solution under commonly encountered industrial conditions, and 3) it is recognized or marketed as a water soluble polymer for a given application by a specific consuming market sector.

In one aspect, a gel comprises at least one polymer having a MW of at least 500 selected from the group consisting of the polyethylene glycol (PEG) series (including PEG 600, PEG 1000, PEG 1500, PEG 15440, PEG 4000, PEG 6000, PEG 9000, PEG 10,000), PEG block copolymers (e.g. PEG-polyoxpropylene block copolymer; PEG-/poly(propylene glycol) triblock copolymers (PEG-PPG-PEG)). PEG's with a low molecular weight, for example PEG20, PEG30, PEG40, PEG60, PEG80, PEG100, PEG115, PEG200, PEG 300, PEG400, have been found to be less suitable for the manufacture of a gel which displays a controlled release of a compound. Thus, a controlled release gel of the invention is distinct from a gel-type polymer solid electrolyte disclosed in Hanabusa et al. (Chem. Mater. 1999, 11, 649-655) comprising a LMWG and a low MW PEG (PEG400).

In another embodiment, the polymer is selected from the dextran series. Dextran is an α-D-1,6-glucose-linked glucan with side-chains 1-3 linked to the backbone units of the Dextran biopolymer. The degree of branching is approximately 5%. The branches are mostly 1-2 glucose units long. The molecular weight of dextran varies normally between 1,000 and 2,000,000 Daltons, all of which may be used when practicing the present invention. Good results were for example obtained using dextran 10,200 or dextran 173,000.

In yet another embodiment, the at least one polymer is methylcellulose (MC) or a derivative thereof, for instance hydroxypropylmethyl-cellulose (HPMC), polyvinylpyrrolidone (PVP), partially hydrolyzed polyvinyl alcohol (PVA), xanthan gum, pullulan or a pullalan derivative. Pullulan is a water soluble, neutral linear polysaccharide consisting of α-1, 4 and α-1,6 glycosidic linkages. Pullulan is produced as a water soluble, extracellular polysaccharide by certain strains of the polymorphic fungus *Aureobasidium pullulans*. Pullulan cannot self-associate in aqueous solution due to its water solubility. Therefore, mostly hydrophobized pullulan derivatives have been used as drug delivery carriers. These hydrophobized pullulan molecules can form relatively monodisperse and colloidally stable nanoparticles (20-30 nm) upon self-aggregation in water.

The term "nonpolymeric gelator" as used herein refers to a low molecular weight gelator, thickener or other type of gelling agent capable of gelating or thickening a solution. Either one of them is herein referred to as "LMWG". A nonpolymeric gelator or thickener of the invention preferably has a molecular weight of less than about 5000 g/mol, more in particular a molecular weight of about 100 to 2000 g/mol. LMWGs are well known in the art. Highly suitable are organo-gelators as described in "Specialist Surfactants" edited by D. Robb of 1997, p 209-263, chapter 8 by P. Terech. In particular the hydroxylated carboxylic fatty acids with a linear or branched aliphatic carbon chain containing in particular at least 8 carbon atoms and preferably at least 12 carbon atoms, such as 12-hydroxystearic acid or 12-hydroxyoleic acid and their salts with alkali metals or alkaline earth metals; the amides of carboxylic acids, in particular tricarboxylic such as the cyclohexane tricatboxamides, resulting from the reaction of cyclohexane tricarboxylic acid and a lauryl amine; ureido derivatives such as the derivatives of 1,2-bis(ureido-)benzene and trans-1,2 bis(ureido)cyclohexane and in particular those described in the article by R. M. Kellogg, B. L. Fering a et al in Chem. Eur. J. 1999.5.No. 3); the esters or amides of valine, and in particular those described in "Specialist Surfactants" (see above); the N-acyl amino acids and derivatives, and in particular the amides of N-acylamino acids such as the diamides resulting from the reaction of an N-acylamino acid with amines containing 1-22 carbon atoms, e.g. those described in WO 93/23008 and in particular the amides of N-acylglutamic acid where the acyl group represents a C8-C22 alkyl chain; the diamides having 1-22 carbon atoms, and preferably 6-18 carbon atoms, the hydrocarbon chains optionally substituted by ester, urea, fluoro groups (See French application no. 009317); amines or amides of steroids and particularly of deoxycholic, cholic, apocholic, lithocholic acids and their salts such as D-17,17-dipropyl-17α-aza-5-homoandrostan-3β-ol 17a-oxy or D-17,17-dipropyl-17α-aza-5-homoandrostan-3β-ol; compounds with several aromatic rings and in particular anthryl derivatives containing at least two alkyl chains having 8-30 carbon atoms such as 2,3-bis-n-decycloxyanthracene, 2,3-bis-n-decycloxyanthraquinon or containing a steroid group such as cholesteryl 4-(2-anthryloxy)butanoate or cholesteryl anthraquinon-2-carboxylaat and their derivatives; the azobenzene steroids such as those described in the book "Specialist Surfactants"; organo-metallic compounds such as mononuclear copper-β-diketonate (the complex of copper octa-substituted with bis(3,4 nonyloxybenzoyl)methanes), the binuclear copper tetracarboxylates or the complexes of Zn(II) with trisubstituted para-carboxyphenyl porphyrin; the surface active agents in the form of salts containing at least two linear or branched alkyl chains and in particular the alkyl phosphates of alkali metals or aluminium containing two alkyl chains having 8-30 carbon atoms such as the aluminium salt of dihexadecyl phosphate (C16) or di(2-ethyl hexyl) sulfosuccinic acid and its alkali metal salts (Na); the benzylidene sorbitols or alditols and derivative such as 1,3:2,4-di-o-benzylidene-D-sorbitol, and their mixtures. In one embodiment, a LMWG is chosen from the group of organogelators, including hydroxylated carboxylic fatty acids, the amides of carboxylic acids such as N,N'dibenzoyl-L-cystine, ureido derivatives, the N-acyl amino acids and derivatives, amines or amides of steroids and amines or amides of sorbitols. For a recent review on LMW hydrogelators see: L. A. Estroff and A. D. Hamilton, Chem. Rev., 2004, 104, 1201-1217.

As is shown in the Examples below, good results were obtained with a controlled release LMWG gel comprising at least one polymer with a molecular weight of at least 500 Dalton in combination with a LMWG having a molecular weight of less than about 5000 g/mol.

The amount of nonpolymeric gelator to be used in the controlled release gel of the invention can vary. It may depend on the type of gelator and/or polymer used, and also on the desired release profile. Generally speaking, the total concentration of gelator in the gel is in the range of about 0.01-20 wt %, preferably about 0.03-10 wt %, more preferably about 0.5-7 wt %.

For preparing a slow-release gel of the invention, good results have been achieved with a gelator represented by the following formula:

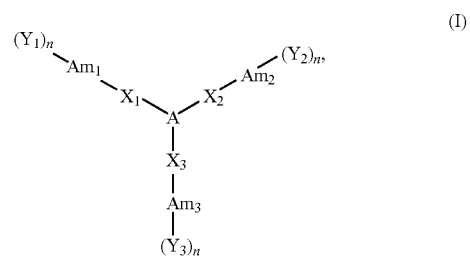

wherein

A represents a cycloalkyl, a heterocycloalkyl, an aromatic or heteroaromatic moiety; each of $X_1$, $X_2$ and $X_3$ is independently chosen from the moieties —N(H)—, —C(O)—, —O(CO)—, —OC(S)—, —C(S)—, —NHC(S)— and —NH—C(O)—;

each of $Am_1$, $Am_2$, and $Am_3$ is independently a moiety based on an amino acid or a derivative thereof, or a number of amino acids or derivatives thereof;

each of $Y_1$, $Y_2$, and $Y_3$ is preferably independently chosen from the group of —OR, —N(OH)R, and —NR$_2$, if the corresponding X ($X_1$ for $Y_1$, $X_2$ for $Y_2$, and $X_3$ for $Y_3$) is —C(O)— or —NH—C(O)— and n=1, and each of $Y_1$, $Y_2$, and $Y_3$ is independently chosen from the group of —C(O)R, —C(O)—NR$_2$, —C(O)—OR, —C(S)R, —C(S)—NR$_2$, —C(S)—OR and R, if the corresponding X ($X_1$ for $Y_1$, $X_2$ for $Y_2$, and $X_3$ for $Y_3$) is —NH— and n=1 or 2.

Each R is independently H, or a substituted or unsubstituted, branched, cyclic or straight alkyl, alkenyl or alkynyl group. The R group preferably has from 1 to 40 carbon atoms and may contain (i.e. may be substituted with) an aromatic, ester and/or an ether moiety and/or one or more other heteroatoms—preferably selected from O, N, P, S and B.

Preferably, each of $X_1$, $X_2$ and $X_3$ is independently chosen from the moieties —NH—, —C(O)—, and —NH—C(O)—;

Each of $Am_1$, $Am_2$, and $Am_3$ is independently a moiety based on an amino acid or a derivative thereof, or a number (e.g. up to 12, up to 6 or up to 3) of amino acids or derivatives thereof. The term "amino acid derivative" as used herein refers to a non-naturally occurring compound having the key structural features of a naturally occurring amino acid: a central chiral carbon (known as the "alpha carbon") that is tetrahedral and chiral (i.e. each of the four functional groups are different) and an amino group and carboxylic acid group. At pH 7.0 these are both (oppositely) charged. The functional group known as the amino acid "side chain" and/or the amino or carboxylic group can be modified, for example protected by BOC or any other protective moiety, methylated, benzoylated. Exemplary amino acid derivatives include Lys(BOC), Ser(benzyl), Asp(OMe), Glu(OMe).

In case A is a (hetero)cycloalkyl, all shown substituents (each X—Am—Y group) are preferably in the equatorial position of the (hetero)cycloalkyl core. In a preferred embodiment, A is a cycloalkyl, more preferably a cyclohexyl. For example, it is a cyclohexylcore that is substituted by $X_1Am_1(Y_1)$., $X_2Am_2(Y_2)$., and $X_3Am_3(Y_3)$, at the 1, 3 and 5 position, respectively.

As indicated above, the R group can be substituted with an aromatic moiety. The term "aromatic" is defined as a group having a set of covalently-bound atoms arranged in one or more rings, which contains a delocalized conjugated π-system, wherein the number of π-delocalized electrons is even, but not a multiple of 4. The aromatic group can be represented as containing an arrangement of alternating single and double bonds. The aromatic ring system may comprise from 5 to 30, preferably from 5 to 18 atoms. The ring system may comprise only carbon atoms. Alternatively, one or more carbon atoms may be substituted by heteroatoms. In this case, the aromatic group may be termed a heteroaromatic group. The one or more heteroatoms may be the same or different. Preferred heteroatoms that can be present in the ring are oxygen, sulfur and nitrogen.

Examples of aromatic groups are phenyl, naphthyl, anthracyl, pyrene, furan, pyridine, pyrazine, pyrrole, imidazole, quinoline, and thiophene.

A further specific embodiment of the invention relates to a slow release gel comprising a non-symmetrical trisubstituted cyclic thickener or gelator wherein A is substituted by one or two X—Am—$Y_n$ groups and wherein the remaining one or two substituents are —X—Z groups, wherein each of X is independently chosen from the moieties —N(H), C(O), O(CO)—, —OC(S)—, —C(S)—, —NHC(S)— and —NH—C(O);

each of Am is independently a moiety based on an amino acid or a derivative thereof, or a number of amino acids or derivatives thereof;

each of Y is independently chosen from the group of OR, —N(OH)R,
—$NR_2$, —C(O)R, C(O)—$NR_2$, C(O)OR, —C(S)R, C(S)—$NR_2$, C(S)—OR and R and n=1 or 2. Each of Y is preferably independently chosen from the group of —OR, —N(OH)R, and —$NR_2$, if the corresponding X is —C(O)— or —NH—C(O)— and n=1, and each of Y is preferably independently chosen from the group of —C(O)R, —C(O)—$NR_2$, —C(O)—OR, —C(S)R, —C(S)—$NR_2$, —C(S)—OR and R, if the corresponding X is —NH— and n=1 or 2.

Each R is independently H, or a substituted or unsubstituted, branched, cyclic or straight alkyl, alkenyl or alkynyl group. The R group preferably has from 1 to 40 carbon atoms and may contain (i.e. may be substituted with) an aromatic, ester and/or an ether moiety and/or one or more other heteroatoms—preferably selected from O, N, P, S and B each Z is independently selected from the group consisting of OH, COOH, C(O)NHR, NHC(O)R and NHR, wherein each R is independently as defined above;

Such a non-symmetrical trisubstituted gelator may be represented by one of the following formulas, wherein A represents the ring (core) of the thickener or gelator and each X, Y, Z respectively Am can represent the same or different X, Y, Z respectively Am.

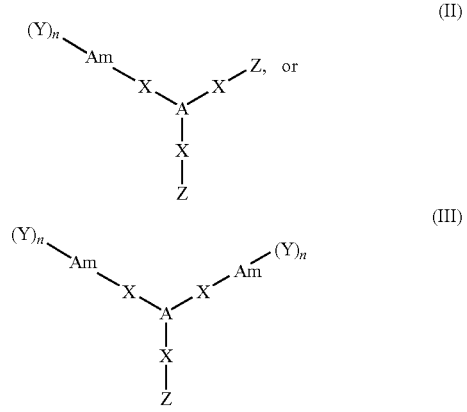

Regarding moieties A, X, Am and Y, the same definitions and preferred embodiments as described in view of Formula I are applicable.

The preparation of a compound according to Formula I, II or III and preferred examples of such compounds are known from International applications WO2003/097587, WO2004/103347 and WO2005/047231 in the name of the applicant, the contents of which are incorporated herein by reference. WO2004/103347 discloses the use of various types of non-polymeric gelators for the formation of nanoparticles of compounds of interest that are poorly soluble in water, for example hydrophobic pharmaceuticals. It does not disclose or suggest the combined use of LMWGs and a non-gelating polymer for the manufacture of a slow release gel.

Of special interest for use in a slow release gel according to the present invention are pH-sensitive gelators that allow for a pH-controlled release of a compound of interest from a slow release gel of the invention. Significant variations in the pH occur in the gastrointestinal tract with values ranging from approximately 1 in the stomach, 6.6 in the proximal small intestine and a peak of about 7.5 in the distal small intestine (Evans et al., 1988, Gut, 29:1035). The pH differential between the stomach and small intestine has historically been exploited to orally deliver drugs to the intestinal tract by way of pH-sensitive polymeric coatings. Delivery of drugs to sites beyond the stomach is especially desirable for drugs that are destroyed by the acid conditions or enzymes of the stomach, or for drugs that cause adverse events by local activity in the stomach. The low stomach pH and presence of gastric enzymes have led to the development of various types of oral drug dosage forms in which the drug is provided with an enteric coating. The present invention now provides a gel-based matrix for the delivery of a compound, e.g. an acid sensitive drug, said matrix comprising a pH-sensitive non-polymeric gelator in combination with at least one polymer. The gel matrix remains essentially intact in an acidic environment but dissolves at a pH>6. The presence of polymer significantly slows down diffusion of the compound during stomach passage, but the gel rapidly degrades in the intestine upon a change in pH. Consequently, there is little or no release during stomach passage but a fast release once the formulation has passed the stomach. Thus, a controlled release gel of the invention that can be triggered by pH is particularly suitable for oral formulations of drugs that degrade during stomach passage. Advantages of these LMWG-based gels over existing polymer gels include in-situ (supramolecular) polymerization, without the need for washing out initiators or catalysts. Furthermore, after a suitable pH trigger the gel rapidly disintegrates into low molecular weight components.

pH-sensitive LMWGs are known in the art, see for example WO2003/084508 in the name of the applicant. In a preferred embodiment, cHex(AmNleOH)$_3$, cHex(AmPheAmGluOH)$_3$, or cHex(AmMetOH)$_3$ is used as acidic gelator (see FIG. 1). WO2003/097587 provides the teaching for the synthesis of such compounds). Ox(Leu)$_2$ described by Makarević et al. (Chem. Eur. J. 2001, 7, 15, 3328-3341) can also be used as an acidic gelator.

According to the invention, many combinations of gelators and polymers can be used for the manufacture of a slow release gel. It is preferred that the at least one gelator and the at least one polymer are compatible with respect to their physicochemical properties, like hydrophilicity, acidity and/or charge. This will allow for interactions between the gel network and the polymer, which interactions can contribute to the dense gel structure. For instance, a hydrophilic gelator is preferably combined with a hydrophilic polymer. Vice versa, hydrophobic polymers are most compatible with hydrophobic gelators. Also, the charge between gelator and polymer should preferably be matching, i.e. non-repellent. In one embodiment, a pH-sensitive gelator and a pH-sensitive polymer are combined to provide a pH-inducible slow release gel. In another embodiment, a pH-sensitive gelator and a pH-insensitive polymer are combined to provide a pH-inducible slow release gel.

In one embodiment, the gel comprises 4 wt % of the gelator cHex(AmPheAmGluOH)$_3$ and 30 wt % of the polymer PEG4000. In another embodiment, the gel comprises 0.5 wt % cHex(AmPheOCH$_2$CH$_2$OCH$_2$CH$_2$OH)$_3$ and 50 wt % PEG4000. In another embodiment, the gel comprises 0.5 wt % cHex(AmPheOCH$_2$CH$_2$OCH$_2$CH$_2$OH)$_3$ and 49 wt % polyvinylpyrrolidone (PVP; MW 29 kDa). In another embodiment, the gel comprises 0.5 wt % cHex (AmPheOCH$_2$CH$_2$OCH$_2$CH$_2$OH)$_3$ and 25 wt % dextran (MW 10.2 kDa). In another embodiment, the gel comprises 0.5 wt % cHex(AmPheOCH$_2$CH$_2$OCH$_2$CH$_2$OH)$_3$ and 15 wt % poly(ethylene glycol)-block-poly(propylene glycol)-block-poly(ethylene glycol) (MW 8.4 kD, 80 wt % PEG) (MW 10.2 kDa).

In yet another embodiment, the gel comprises 0.5 wt % cHex(AmMetOH)$_3$ and 25 wt % PEG4000. In another embodiment, the gel comprises 0.5 wt % cHex(AmMetOH)$_3$ and 25 wt % PVP. In another embodiment, the gel comprises 0.5 wt % cHex(AmMetOH)$_3$ and 25 wt % dextran (MW 10.2 kDa). In another embodiment, the gel comprises 0.5 wt % cHex(AmMetOH)$_3$ and 15 wt % polymer poly(ethylene glycol)-block-poly(propylene glycol)-block-poly(ethylene glycol) (MW 8.4 kD, 80 wt % PEG) (MW 10.2 kD).

As indicated above, slow release or controlled release gels of the invention are particularly suitable for the delivery of a compound to a target site. Provided herein is a gel according to the invention, further comprising at least one compound of interest. The compound of interest can be a biologically active molecule. Preferably, it is a pharmaceutical (drug) or a cosmetic compound. A gel may comprise any type of molecule whose incorporation into the gel contributes to a desired targeting specificity of the molecule, lowering systemic drug toxicity, improving treatment absorption rates, and/or providing protection for pharmaceuticals against biochemical degradation.

Figure 2:
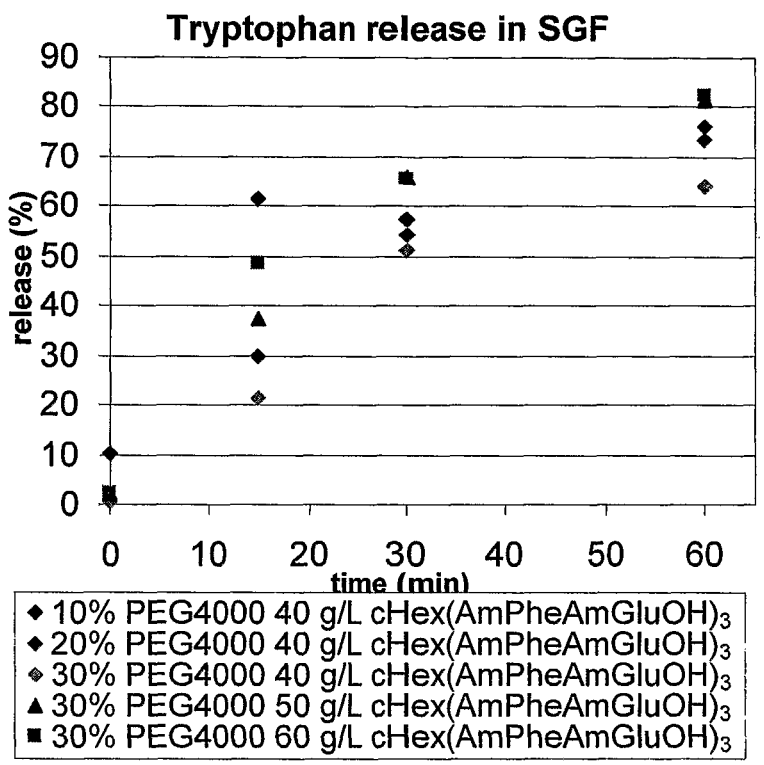

The compound of interest is for example selected from the group consisting of peptides, peptide drugs, proteins, protein drugs, therapeutic antibodies, desensitizing agents, antigens, vitamins, vaccines, anti-infectives, antibiotics, antimicrobials, antineoplastics, antitumor drugs, antiallergenics, steroidal anti-inflammatory agents, analgesics, decongestants, miotics, anticholinergics, sympathomimetics, sedatives, hypnotics, antipsychotics, psychic energizers, tranquilizers, androgenic steroids, estrogens, progestational agents, humoral agents, prostaglandins, analgesics, antispasmodics, antimalarials, antihistamines, cardioactive agents, non-steroidal anti-inflammatory agents, antiparkinsonian agents, antihypertensive agents, beta-adrenergic blocking agents, nutritional agents, antivirals, nucleic acids (genetic material, oligonucleotides), radioisotopes, or combinations of these classes of compounds or other forms such as uncharged molecules, molecular complexes, salts, ethers, esters, amides, and other chemically modified forms of the biologically active agent which are biologically activated following administration into the body, anti-ageing agents, anti-oxidants and skin whitening agents. In one embodiment, the compound of interest is a proteinacous substance. FIG. 2 demonstrates the slow release of an amino acid and FIG. 4 demonstrates the slow release of a protein (Cytochrome C).

A further aspect of the invention relates to a method for preparing a gel according to the invention. Conventional methods for preparing a gel can be used, including solvent change or temperature quench methods. In one embodiment, it comprising the steps of providing a solution of at least one polymer in an amount of more than 5% by weight and, optionally, a compound of interest, in a solvent; and inducing thickening or gelation of said solution using at least one nonpolymeric gelator to produce a thickened solution or gel. The solvent can be an aqueous or a non-aqueous solvent. In another embodiment, it comprises the steps of providing a solution of at least one nonpolymeric gelator in a solvent; and inducing gelation or thickening by mixing the solution with a non-solvent, wherein the at least one polymer and/or the compound of interest may be present in the solvent and/or in the non-solvent. Other methods may however also be used, for example wherein first a gel is prepared and wherein subsequently a compound of interest is incorporated. The experimental section below provides examples of how gels of the invention are suitably prepared.

The semi-solid gel thus obtained can be used as such in a controlled delivery system. Alternatively, the gel can be dried to form a solid and/or particulate form of the gel. It was found that also in a dried form a gel of the invention is suitable as controlled release system. Drying of the gel to obtain a particulate gel can be accomplished by several methods known in the art, including solvent evaporation, freeze drying, spray drying or by centrifugation. Freeze-drying is preferred. The dried gel composition can be incorporated into conventional drug formulations, like a tablet, capsule or pill.

In a further embodiment, the invention provides a system for the controlled release, access or delivery of a compound of interest, comprising a gel according to the invention. Compared to existing LMWG gels, a system of the invention comprises a gel with increased mechanical strength (see Examples 1-6). The release of an enclosed compound from a gel is controlled by a trigger, such as by a chemical or physical trigger. Preferably, release is controlled by pH, electromagnetic radiation, temperature, electricity, the presence of (metal) ions, the presence of oxidizing or reducing species, an enzymatic reaction, and/or sonication. Suitable examples of gelators whose gels can be triggered by pH can be found in WO2003/097587, and WO2005/047231 by the applicants. Van Bommel et al. (Organic & Biomolecular Chemistry, 2005, 3(16), 2917-2920) described a release system controlled by an enzymatic reaction. An example of switching of a gel by electromagnetic radiation (light) is described by De Jong et al. (Science, 2004, 304(5668), 278-281). The system is for example a drug delivery system, like a pH-controlled drug delivery system.

In a specific aspect, the invention provides a bioadhesive delivery system. The term "bioadhesive" refers to materials, e.g a slow release gel of the invention, that can bind to biological substrates, such as mucosal membranes. Adhesion of a bioadhesive drug delivery device to mucosal membranes leads to an increased drug concentration gradient at the absorption site and therefore to improved bioavailability. Mucosal targeting sites include the eye, oral cavity, nasal cavity, GI tract and vagina. Bioadhesive dosage forms are particularly suitable to target local disorders at the mucosal surface to reduce the overall dosage required and to minimise side-effects that may be caused by systemic administration of drugs. Bioadhesive formulations typically use polymers as the adhesive component. Bioadhesive polymers that can be used to prepare a bioadhesive slow-release gel of the invention include crosslinked polyacrylic acid and poly(ethyleneoxide). The gel can be used in a bioadhesive delivery system for the delivery of a compound of interest to the eye, GI tract, oral cavity and other mucosal sites of interest. In a specific embodiment, the invention provides a LMWG-gel based bioadhesive system that adheres to the mucosal surface and provides for a slow release of a vaccine, e.g. in the nasal or oral cavity. Herewith, the invention also provides a pharmaceutical composition comprising a gel or a (bioadhesive) delivery system according to the invention. Of course, the composition can be a prophylactic or therapeutic composition. In a specific aspect a cosmetic composition is provided, for example for delivery of an anti-ageing compound, a skin whitening agent, and/or an anti-oxidant.

Also provided herein is a method of treatment, comprising administering to a subject in need thereof a pharmaceutical composition according to the invention comprising a slow release gel wherein enclosed at least one therapeutically active compound. In one embodiment, it is a method to relieve pain comprising administering a composition comprising a pain-killer enclosed in a gel according to the invention. The gel for instance comprises an acidic gelator which protects the pain-reliever during passage through the stomach yet which rapidly releases the drug once the pH is sufficiently high to dissolve the gel network.

LEGENDS TO THE FIGURES

Figure 3:
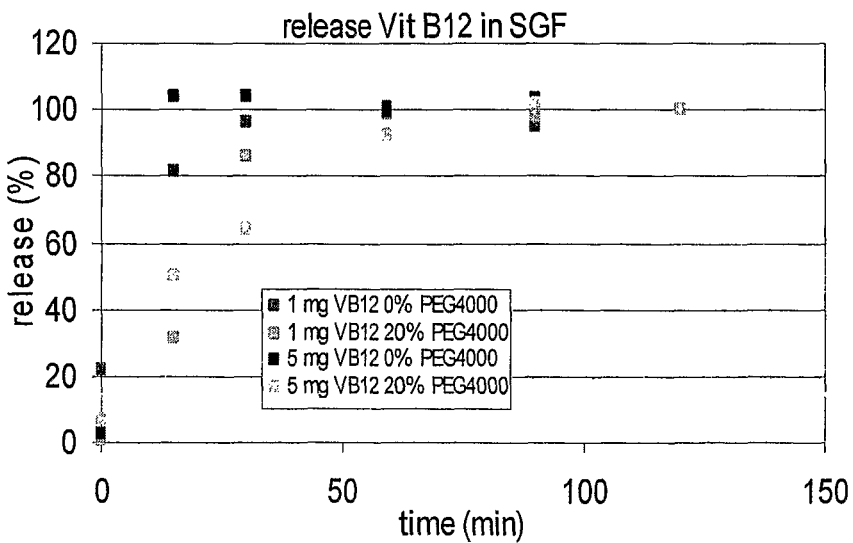
Figure 4:
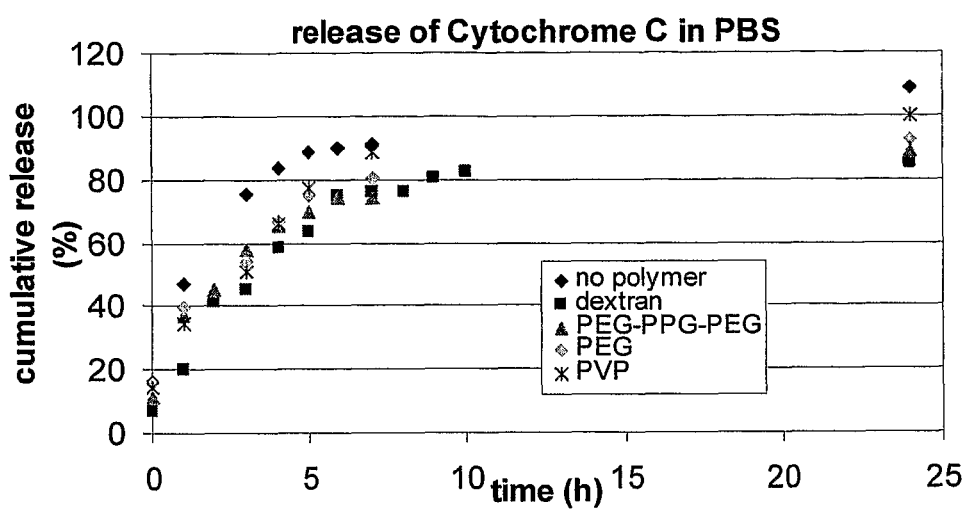

FIG. 1: Nonpolymeric gelator structures
FIG. 2: Release of tryptophan from 0.5 mL gel containing 5 mg/mL tryptophan into 2 mL SGF (pH 1.2).
FIG. 3: Release of Vitamin B12 from PEG4000-containing hydrogels.
FIG. 4: Release of Cytochrome C from various hydrogels.

EXPERIMENTAL SECTION

Example 1

To 2.5 mg ($2.7 \times 10^{-3}$ mmol) of cHex(AmPheOCH$_2$CH$_2$OCH$_2$CH$_2$OH)$_3$ (FIG. 1), 500 µL water (A), or 500 µL of a 50% (w/v) solution of polyethylene glycol (PEG4000; MW 4 kD) in water (B), or 500 µL of a 49% (w/v) solution of polyvinylpyrrolidone (MW 29 kD) in water (C) were added. The samples were heated until complete dissolution of the gelator was achieved and were then allowed to cool and thus gel. The firmness of the resulting gels was estimated by attempting to break them up by vortexing for a maximum of 30 seconds (s). The break-up times were 4 s, >30 s, >30 s for gels (A), (B) and (C), respectively.

Example 2

To 2.5 mg ($3.8 \times 10^{-3}$ mmol) of cHexAm(PheAmAQ)(CH$_2$CH$_2$OCH$_2$CH$_2$OH)$_2$ (FIG. 1), 500 µL of water (A), or 500 µL of a 25% (w/v) solution of dextran (W 10.2 kD) in water (B), or 500 µL of a 50% (w/v) solution of dextran (MW 10.2 kD) in water (C) were added. The samples were heated until complete dissolution of the gelator was achieved and were then allowed to cool and thus gel. The firmness of the resulting gels was estimated by attempting to break them up by vortexing for a maximum of 30 s. The break-up times were 8 s (A), >30 s (B), >30 s (C).

Example 3

To 2.5 mg ($3.9 \times 10^{-3}$ mmol) of cHexAm(PheAmCH$_2$CH$_2$Ph)(CH$_2$CH$_2$OCH$_2$CH$_2$OH)$_2$ (FIG. 1), 500 µL of water (A), or 500 µL of a 30% (w/v) solution of poly(ethylene glycol)-block-poly(propylene glycol)-block-poly(ethylene glycol) (MW 8.4 kD, 80 wt % PEG) in water (B), or 500 µL of a 49% (w/v) solution of polyvinylpyrrolidone (MW 29 kD) in water (C) were added. The samples were heated until complete dissolution of the gelator was achieved and were then allowed to cool and thus gel. The firmness of the resulting gels was estimated by attempting to break them up by vortexing for a maximum of 30 s. The break-up times were 4 s (A), >30 s (B), >30 s (C).

Example 4

To 2.5 mg ($4.5 \times 10^{-3}$ mmol) of cHex(AmNleOH)$_3$ (FIG. 1), 500 µL of water (A), or 500 µL of a 2.5% (w/v) solution of chitosan (medium MW, Aldrich, Product number 448877) in water (B), or 500 µL of a 6% (w/v) solution of chitosan (medium MW) in water (C) were added. The samples were heated until complete dissolution of the gelator was achieved and were then allowed to cool and thus gel. The firmness of the resulting gels was estimated by attempting to break them up by vortexing for a maximum of 30 s. The break-up times were 13 s (A), 1 s (B), >30 s (C).

Example 5

To 2.5 mg ($3.0 \times 10^{-3}$ mmol) of cHexAmNleOCH$_2$CH$_2$OCH$_2$CH$_2$OH (FIG. 1), 500 µL of water (A), or 500 µL of a 49% (w/v) solution of polyvinylpyrrolidone (MW 29 kD) in water (B) were added. The samples were heated until complete dissolution of the gelator was achieved and were then allowed to cool and thus gel. The firmness of the resulting gels was estimated by attempting to break them up by vortexing for a maximum of 30 s. The break-up times were 4 s (A), >30 s (B).

Example 6

To 5 mg ($1.6 \times 10^{-2}$ mmol) of Ox(AmLeu)$_2$ (FIG. 1), 500 µL of water (A), or 500 µL of a 30% (w/v) solution of poly(ethylene glycol)-block-poly(propylene glycol)-block-poly(ethylene glycol) (MW 8.4 kD, 80 wt % PEG) in water (B), or 500 µL of a 49% (w/v) solution of polyvinylpyrrolidone (MW 29 kD) in water (C) were added. The samples were heated until complete dissolution of the gelator was achieved and were then allowed to cool. The composition of (A) resulted in a clear solution, samples (B) and (C) formed gels. The firmness of the gels was estimated by attempting to break them up by vortexing for a maximum of 30 s. The break-up times were >30 s (B), >30 s (C).

Example 7

40.4 mg ($39 \times 10^{-3}$ mmol) of cHex(AmPheAmGluOH)$_3$, 4.9 mg ($24 \times 10^3$ mmol) of tryptophan, 100 mg of PEG4000, and 900 µL of water (A), or 39.9 mg ($38 \times 10^{-3}$ mmol) of cHex(AmPheAmGluOH)$_3$, 5.1 mg ($25 \times 10^{-3}$ mmol) of tryptophan, 200 mg of PEG4000, and 800 µL of water (B), or 39.9 mg ($38 \times 10^{-3}$ mmol) of cHex(AmPheAmGluOH)$_3$, 5.0 mg ($24 \times 10^{-3}$ mmol) of tryptophan, 300 mg of PEG4000, and 700 µL of water (C), or 50.0 mg ($48 \times 10^{-3}$ mmol) of cHex(AmPheAmGluOH)$_3$, 4.9 mg ($24 \times 10^{-3}$ mmol) of tryptophan, 300 mg of PEG4000, and 700 µL of water (D), or 61.4 mg ($59 \times 10^{-3}$ mmol) of cHex(AmPheAmGluOH)$_3$, 5.0 mg ($24 \times 10^{-3}$ mmol) of tryptophan, 300 mg of PEG4000, and 700 µL of water (E) were heated until complete dissolution of both the gelator and the tryptophan was achieved and were then allowed to cool and thus gelate.

Example 8

164 mg (157×10⁻³ mmol) of cHex(AmPheAmGluOH)$_3$ was dissolved in 820 µl 1 N aqueous NaOH. 200 µl of this stock solution was added to vortexed solutions containing 1.1 mg Vitamin B12 ($8.1\times10^{-4}$ mmol), 600 µl water, and 200 µl 1 N aqueous HCl (A), or 1.1 mg Vitamin B12 ($8.1\times10^{-4}$ mmol), 200 mg PEG4000, 400 µl water, and 200 µl 1 N aqueous HCl (B), or 5.0 mg Vitamin B12 ($3.6\times10^{-3}$ mmol), 600 µl water, and 200 µl 1 N aqueous HCl (C), or 5.1 mg Vitamin B12 ($3.8\times10^{-3}$ mmol), 200 mg PEG4000, 400 µl water, and 200 µl 1 N aqueous HCl (D). Gelation occurred as soon as vortexing was stopped.

Example 9

An amount of 500 µL of a 1 wt % aqueous solution of the dye Evan's blue was carefully placed on top of gels of 2.5 mg ($2.7\times10^{-3}$ Mmol) of cHex(AmPheOCH$_2$CH$_2$OCH$_2$CH$_2$OH)$_3$ (FIG. 1) in 500 µL of water (A), or 500 µL of a 50% (w/v) aqueous solution of polyethylene glycol (MW 4 kD) (B), or 500 µL of a 49% (w/v) aqueous solution of polyvinylpyrrolidone (MW 29 kD) (C)), or 500 µL of a 25% (w/v) aqueous solution of dextran (MW 10.2 kD) (D), or 500 µL of a 15% (w/v) solution of poly(ethylene glycol)-block-poly(propylene glycol)-block-poly(ethylene glycol) (MW 8.4 kD, 80 wt % PEG) in water (E). All gels were prepared by heating until complete dissolution had occurred and subsequent cooling. The blue color diffused throughout all parts of the gel in 5 h (A), 24 h (B), 48 h (C), 19 h (D), 24 h (E).

Example 10

An amount of 500 µL of a 1 wt % aqueous solution of Evan's blue was carefully placed on top of gels of 5.0 mg ($8.2\times10^{-3}$ mmol) of cHex(AmMetOH)$_3$ (FIG. 1) in 500 µL of water (A), or 500 µL of a 25% (w/v) aqueous solution of polyethylene glycol (MW 4 kD) (B), or 500 µL of a 25% (w/v) aqueous solution of polyvinylpyrrolidone (MW 29 kD) (C), or 500 µL of a 25% (w/v) aqueous solution of dextran (MW 10.2 kD) (D), or 500 µL of a 15% (w/v) solution of poly(ethylene glycol)-block-poly(propylene glycol)-block-poly(ethylene glycol) (MW 8.4 kD, 80 wt % PEG) in water (E). All gels were prepared by heating until complete dissolution had occurred and subsequent cooling. The blue color diffused throughout all parts of the gel in 4 h (A), 24 h (B), 24 h (C) 24 h (D), 24 h (E).

Example 11

Release of Tryptophan from LMWG-PEG Hydrogels

Hydrogels containing 5 mg/mL tryptophan and varying amounts of non-polymeric acidic gelator cHex(AmPheAmGluOH)$_3$ and polymer PEG4000 were prepared according to Example 8. The release of tryptophan from the gels into simulated gastric fluid (SGF; pH 1.2 was followed using UV (FIG. 2). The initial rate of tryptophan release was found to be much lower in gels containing at least 20% PEG4000. Increasing the cHex(AmPheAmGluOH)$_3$ concentration from 4 to 6% (w/v) did not improve the delay of the release. After incubation in SIF (pH 6.8) for 10 minutes, all remaining tryptophan is recovered. This experiment demonstrates that the incorporation of a polymer into a LMWG gel can significantly delay the release of an enclosed low molecular weight compound from the gel.

Example 12

Release of Vitamin B12 from Gel into Simulated Gastric Fluid

Hydrogels containing 1 or 5 mg/mL Vitamin B12, 40 mg/mL gelator cHex(AmPheAmGluOH)$_3$ and 0% or 20% PEG4000 were prepared. The release of Vitamin B12 from the gels into simulated gastric fluid (SGF; pH 1.2) was followed using UV (FIG. 3). Addition of polymer to the gel clearly retarded the initial release rate of vitamin B12.

Example 13

Preparation of Various Hydrogels Comprising Cytochrome C

A solution containing 1.25 mg Cytochrome C (from bovine heart) and 800 µl phosphate buffered saline (PBS; pH 7.4) (A), or 1.04 mg Cytochrome C, 160 mg dextran (MW 15 kD), and 800 µl PBS (B), or 1.04 mg Cytochrome C, 160 mg PEG4000, and 800 µl PBS (C), or 1.04 mg Cytochrome C, 160 mg poly(ethylene glycol)-block-poly(propylene glycol)-block-poly(ethylene glycol) (MW 8.4 kD, 80 wt % PEG), and 800 µl PBS (D), or 1.04 mg Cytochrome C, 160 mg polyvinylpyrrolidone (MW 29 kD), and 800 µl PBS (E) was quickly added to a solution containing 10 mg ($1.1\times10^{-5}$ mol) cHex(AmPheOEtOEtOH)$_3$ (FIG. 1), 133 µl EtOH, and 67 µl H$_2$O, that was kept at 50° C. Gelation occurred immediately after addition of the Cytochrome C solutions.

Example 14

Release of Cytochrome C from Various Hydrogels

Hydrogels containing 1.04 mg/mL Cytochrome C and varying types of polymers plus LMWG cHex(AmPheOEtOEtOH)$_3$ (FIG. 1) were prepared according to Example 13. The release of Cytochrome C from the gels into 15 mL PBS in a shaking incubator (100 rpm, 37° C.) was followed using UV (FIG. 4). At different time points small aliquots (0.5 ml) were taken from the samples and replaced with fresh PBS. The aliquots were filtered, DTT was added, and the Cytochrome C concentration was determined from the UV absorbance at 413 nm. The data demonstrate the delay in release of Cytochrome C from the gels upon addition of polymer.

The invention claimed is:
1. A sustained release gel comprising:
   (i) from 0.01-20 weight percent (wt %) of at least one low molecular weight gelator having a molecular weight of less than about 5000 g/mol and able to form a self-assembled, thermoreversible, viscoelastic material, and
   (ii) at least 20 wt % of at least one polymer having a molecular weight of at least 500 Da.
2. The sustained release gel of claim 1, wherein the gelator has a molecular weight of about 100 to 2000 g/mol.
3. The sustained release gel of claim 1, wherein the polymer has a molecular weight of at least 1 kDa or at least 1.5 kDa.
4. The sustained release gel of claim 1, wherein the polymer is a grafted, branched, linear polymer, or wherein the gel comprises a mixture of a grafted, branched and/or linear polymers.

5. The sustained release gel of claim 1, wherein the polymer is biocompatible and/or biodegradable.

6. The sustained release gel of claim 1, wherein the polymer is selected from the group consisting of PEG series, dextran series, methylcellulose (MC), MC derivatives, polyvinylpyrrolidone (PVP), partially hydrolyzed polyvinyl alcohol (PVA), xanthan gum, and pullulan.

7. The sustained release gel of claim 1, wherein the gelator is an organogelator.

8. The sustained release gel of claim 7, wherein the organogelator is selected from the group consisting of hydroxylated carboxylic fatty acids, the amides of carboxylic acids, N,N'dibenzoyl-L-cystine, ureido derivatives, N-acyl amino acids, N-acyl amino acids derivatives, amines or amides of steroids, and sorbitols.

9. The sustained release gel of claim 1, wherein the gelator is a pH-sensitive, an electromagnetic radiation sensitive, a temperature sensitive, an electricity sensitive, and/or sonication sensitive gelator, and/or a gelator sensitive to ions or metal ions, oxidation, reduction, and/or enzymatic reaction.

10. The sustained release gel of claim 1, wherein the gelator is a gelator of formula I:

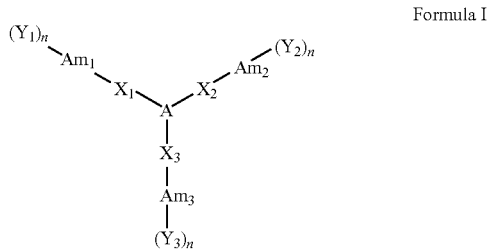

Formula I wherein
A represents a cycloalkyl, a heterocycloalkyl, an aromatic or heteroaromatic moiety;
each of $X_1$, $X_2$ and $X_3$ is independently selected from the group consisting of —N(H)—, —C(O)—, —O(CO)—, —OC(S)—, —C(S)—, —NHC(S)— and —NH—C(O)—;
each of $Am_1$, $Am_2$, and $Am_3$ is independently a moiety based on an amino acid or a derivative thereof, or a number of amino acids or derivatives thereof;
each of $Y_1$, $Y_2$, and $Y_3$ is independently selected from the group consisting of —OR, —N(OH)R, and —NR$_2$, if the corresponding X ($X_1$ for $Y_1$, $X_2$ for $Y_2$, and $X_3$ for $Y_3$) is —C(O)— or —NH—C(O)— and n=1, and each of $Y_1$, $Y_2$, and $Y_3$ is independently selected from the group consisting of —C(O)R, —C(O)—NR$_2$, —C(O)—OR, —C(S)R, —C(S)—NR$_2$, —C(S)—OR and R, if the corresponding X ($X_1$ for $Y_1$, $X_2$ for $Y_2$, and $X_3$ for $Y_3$) is —NH— and n=1 or 2, wherein each R is independently H, or a substituted or unsubstituted, branched, cyclic or straight alkyl, alkenyl or alkynyl group which possibly contains an aromatic, ester or ether moiety or one or more other heteroatoms and may have from 1 to 40 carbon atoms; and
n is 1 or 2.

11. The sustained release gel of claim 1, wherein the gelator is a non-symmetrical, trisubstituted cyclic gelator, of which the ring is substituted by one or two X Am Yn groups and wherein the remaining one or two substituents are —XZ groups, as shown in formula II or formula III

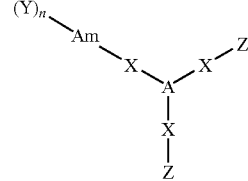

Formula II

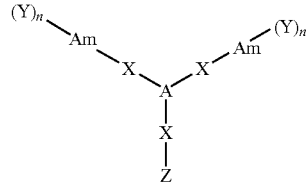

Formula III wherein
each of X is independently selected from the group consisting of —N(H), C(O), O(CO), OC(S), C(S), —NHC(S) and —NH—C(O);
each of Am is independently a moiety based on an amino acid or a derivative thereof, or a number of amino acids or derivatives thereof;
each of Y is independently selected from the group consisting of OR, N(OH)R, NR2, —C(O)R, C(O)—NR2, C(O) OR, —C(S)R, C(S)—NR2, C(S)—OR and R, if the corresponding X ($X_1$ for $Y_1$, $X_2$ for $Y_2$, and $X_3$ for $Y_3$) is —NH— and n=1 or 2, wherein each R is independently H, or a substituted or unsubstituted, branched, cyclic or straight alkyl, alkenyl or alkynyl group which optionally contains an aromatic, ester or ether moiety or one or more other heteroatoms and optionally has from 1 to 40 carbon atoms,
each Z is independently selected from the group consisting of OH, COOH, C(O)NHR, NHC(O)R, and NHR, wherein R, if the corresponding X ($X_1$ for $Y_1$, $X_2$ for $Y_2$, and $X_3$ for $Y_3$) is —NH— and n=1 or 2, wherein each R is independently H, or a substituted or unsubstituted, branched, cyclic or straight alkyl, alkenyl or alkynyl group which possibly contains an aromatic, ester or ether moiety or one or more other heteroatoms and may have from 1 to 40 carbon atoms; and n=1 or 2.

12. The sustained release gel of claim 1, further comprising at least one compound of interest.

13. The sustained release gel of claim 12, wherein the gel is dried.

14. A method for preparing the sustained release gel of claim 1, the method comprising the steps of:
providing a solution of at least one polymer having a molecular weight of at least 500 Da in an amount of more than 20 wt % and, optionally, a compound of interest, in a solvent; and
inducing thickening or gelation of the solution to produce a sustained release gel utilizing from 0.01-20 wt % of at least one gelator having a molecular weight of less than about 5000 g/mol.

15. A method for preparing the sustained-release gel of claim 1, the method comprising the steps of:
providing a solution of from 0.01-20 wt % of at least one gelator in a solvent, the gelator being a low molecular weight gelator having a molecular weight of less than about 5000 g/mol and able to form a self-assembled, thermoreversible, viscoelastic material, gelator being an organogelator; and inducing gelation or thickening by mixing the solution with a non-solvent, wherein at least one polymer and/or a compound of interest may be present in the solvent and/or in the non-solvent, provided that the total amount of polymer is more than 20 wt %.

16. A method for drying a gel, the method comprising:
providing the sustained release gel of claim 12, and
drying the gel,
wherein the drying comprises freeze-drying, spray drying or solvent evaporation.

17. A system for the controlled delivery of a compound of interest, the system comprising:
the sustained release gel of claim 12, and
an environment suitable for delivery of the compound of interest to the environment.

18. The system of claim 17, wherein delivery of the compound of interest is controlled by pH, electromagnetic radiation, temperature, electricity, presence of ions or metal ions, presence of oxidating or reducing species, enzymatic reaction, and/or sonication.

19. A cosmetic or pharmaceutical composition comprising the sustained release gel of claim 1.

20. A method of medical or cosmetic treatment, the method comprising:
administering to a subject in need thereof the system of claim 18.

21. The sustained release gel of claim 12, wherein the compound of interest is selected from the group consisting of a peptide, a protein, a therapeutic antibody, a desensitizing agent, an antigen, a pharmaceutical composition, a cosmetic compound, a vitamin, vaccine, anti-infective, antibiotic, anti-microbial, anti-neoplastic, anti-tumor drug, anti-allergenic, steroidal anti-inflammatory agent, analgesic, decongestant, miotic, anticholinergic, sympathomimetic, sedative, hypnotic, antipsychotic, tranquilizer, androgenic steroid, estrogen, progestational agent, prostaglandin, antispasmodic, anti-malarial, antihistamine, cardioactive agent, non-steroidal anti-inflammatory agent, anti-Parkinson's agent, antihypertensive agent, beta-adrenergic blocking agent, nutritional agent, antiviral, nucleic acid, oligonucleotide, radioisotope, anti-ageing agents, anti-oxidants, a combination of any thereof, other form of any thereof, uncharged molecules, molecular complex thereof, salt thereof, ether thereof, ester thereof, and amide thereof.

22. A sustained release gel comprising:
(i) from 0.01-20 weight percent (wt %) of at least one low molecular weight gelator having a molecular weight of less than about 5000 g/mol and able to form a self-assembled, thermoreversible, viscoelastic material, and
(ii) at least 30 wt % of at least one polymer having a molecular weight of at least 500 Da.

* * * * *